United States Patent [19]

Venkat et al.

[11] Patent Number: 4,549,815

[45] Date of Patent: Oct. 29, 1985

[54] MEASUREMENT OF IGNITION CHARACTERISTICS OF DISTILLATE FUELS

[75] Inventors: Chaya Venkat, Bellemead, N.J.; Dennis E. Walsh, Richboro, Pa.

[73] Assignee: Mobil Oil Corporation, New York, N.Y.

[21] Appl. No.: 554,014

[22] Filed: Nov. 21, 1983

[51] Int. Cl.[4] .............................................. G01N 25/54
[52] U.S. Cl. ........................................ 374/8; 374/143; 374/170; 436/156
[58] Field of Search ...................... 374/8, 39; 436/156, 436/155

[56] References Cited

U.S. PATENT DOCUMENTS

| 3,408,856 | 11/1968 | Gross | 374/8 X |
| 3,670,561 | 6/1972 | Hundere | 374/8 X |
| 3,985,505 | 10/1976 | Bredeweg | 436/155 X |
| 3,987,661 | 10/1976 | Kamp et al. | 374/8 |
| 4,229,181 | 10/1980 | Espitalie et al. | 436/155 X |

FOREIGN PATENT DOCUMENTS

| 0019008 | of 1908 | United Kingdom | 436/156 |
| 0394736 | 7/1933 | United Kingdom | 436/156 |

*Primary Examiner*—Daniel M. Yasich
*Attorney, Agent, or Firm*—Alexander J. McKillop; Michael G. Gilman; Charles J. Speciale

[57] ABSTRACT

Ignition delay of distillate fuels is measured by heating a block to an elevated temperature and injecting samples into a cavity in the block as it cools. The time between each injection and ignition of the fuel is measured. This measurement of ignition delay is used to determine the cetane number of the distillate fuel.

8 Claims, 5 Drawing Figures

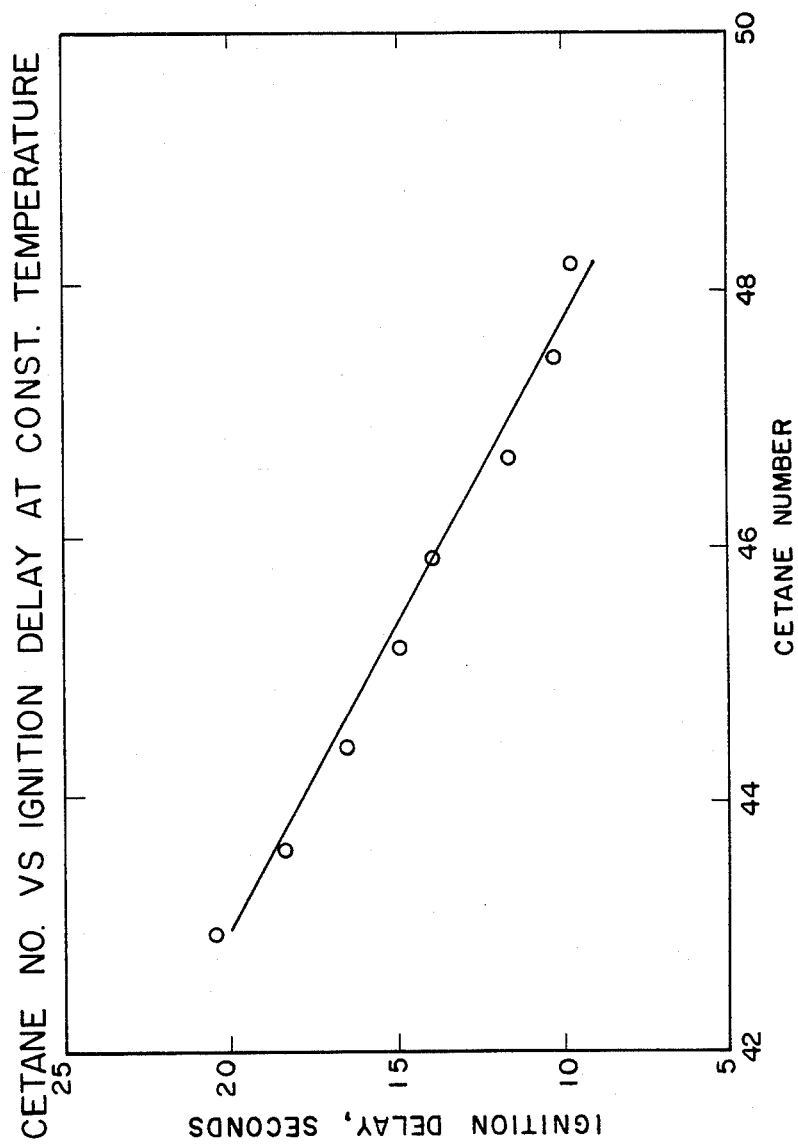

MEASUREMENT OF IGNITION CHARACTERISTICS OF DISTILLATE FUELS

BACKGROUND OF THE INVENTION

This invention relates to apparatus and methods for rapidly determining the ignition behavior of distillate fuels and more particularly to the measurement of ignition delay as a function of temperature.

The ignition quality of distillate fuels is defined by several parameters, one of which is the cetane number. Cetane number measurements are described, for example, in ASTM STANDARD TEST METHOD FOR IGNITION QUALITY OF DIESEL FUELS.

Prior workers have observed that fuels having a low cetane number often have a high ignition delay, which is the time between when a fuel is exposed to an ignition temperature and its ignition. See R. W. Hurn and K. J. Hughes, "Combustion Characteristics of Diesel Fuel as Measured in a Constant Volume Bomb, S.A.E. Quarterly Transactions, Vol. 6, No. 1, 1952.

However, the prior art has not attempted to measure cetane number by measuring ignition delay because ignition delay measurement techniques do not provide the level of accuracy and reproducibility which is required for the rapid comparison of the relative ignition behavior of distillate fuel samples and for the estimation of their absolute cetane number. It is desirable to provide a rapid, accurate technique for accessing the ignition properties of fuels for products and process research and development work and in refinery operations as a quality control guide. Such a tool could be useful in terminal operations and by large volume purchasers wishing to check fuel quality.

SUMMARY OF THE INVENTION

In accordance with the present invention, the ignition delay of distillate fuel is measured by apparatus which includes a block having an ignition cavity. The block is heated to an elevated temperature above the ignition temperature of the fuel and then allowed to cool slowly. As it cools, samples of fuel are injected into the ignition cavity at times which are controlled by a digital computer. A pressure transducer and a thermocouple measure the pressure and temperature, respectively, in the cavity. For each injected sample, the digital computer measures ignition delay as the time between injection of a sample and ignition as indicated by a peak in measured cavity pressure or cavity temperature. The ignition delay is recorded as a function of the cavity temperature prior to fuel injection.

Using the temperature required for a given ignition delay, the cetane rating of distillate fuels may be estimated from a calibration curve established by comparing unit data with results from the ASTM cetane number test. It has been found that the ignition temperatures of the tested distillate fuels fall on a smooth correlation curve which can be used to provide cetane number estimates for unknown fuels. These are in excellent agreement with observed ASTM values.

The foregoing and other objects, features and advantages of the invention will be better understood from the following more detailed description and appended claims.

SHORT DESCRIPTION OF THE DRAWINGS

FIG. 5 shows the ignition delay in seconds as a function of the cetane number.

DESCRIPTION OF THE PREFERRED EMBODIMENT

Figure 1:
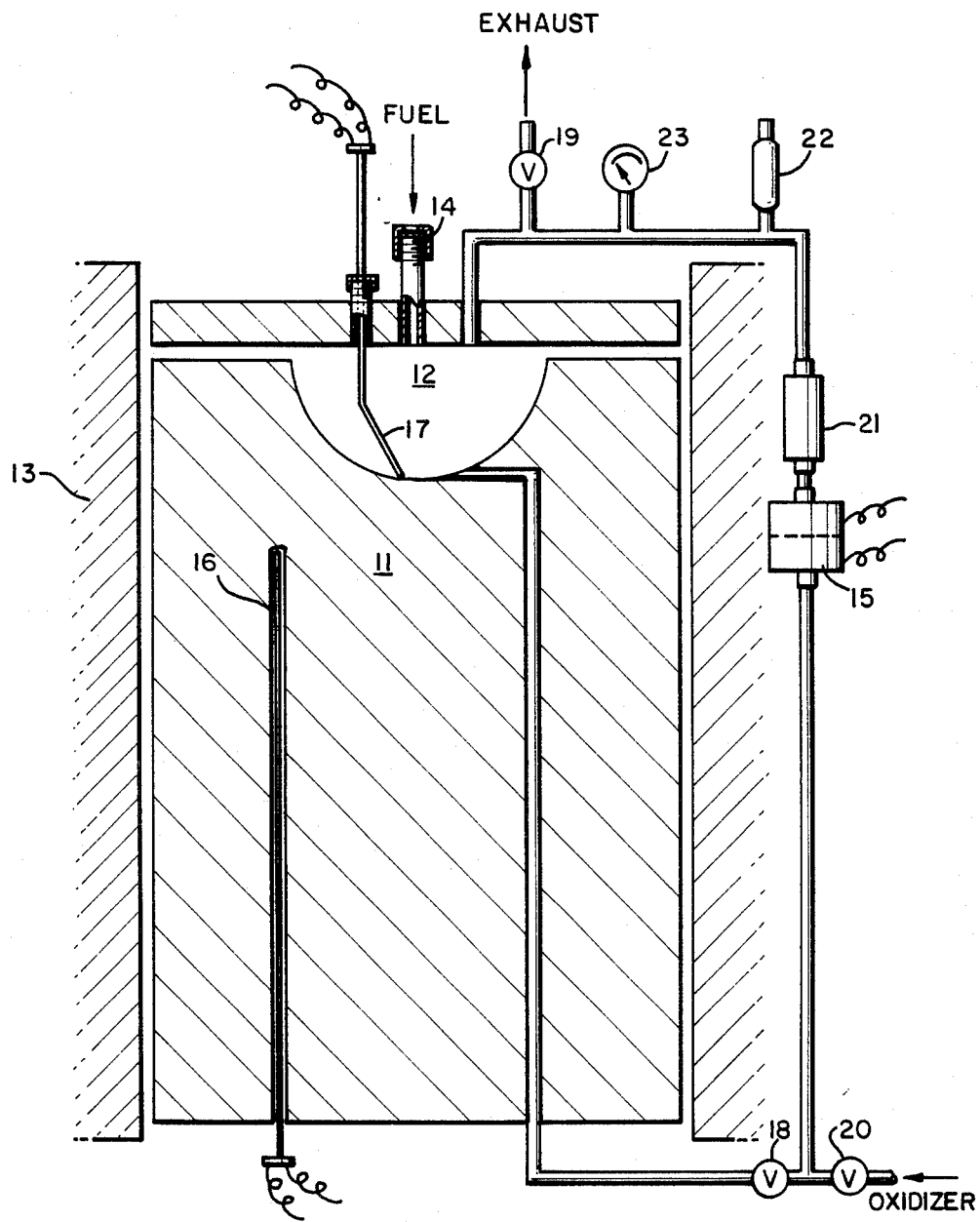
FIG. 1 depicts the block and ignition cavity.

Referring to FIG. 1, the ignition delay of a distillate fuel is measured by an apparatus which includes a block 11 having an ignition cavity 12. A heater 13 heats the block to an elevated temperature above the ignition temperature of the fuel. An injector injects samples of fuel through injection port 14 into the ignition cavity as the block cools from the elevated temperature. Pressure transducer 15 measures the pressure in the cavity. Thermocouples 16 and 17 measure the temperature in the block and the cavity respectively.

Solenoid valve 18 is connected between a source of oxygen and the ignition cavity 12 to flush it with oxygen which is exhausted through the solenoid actuated valve 19. Solenoid valve 20 supplies oxygen to one side of pressure transducer 15. A pressure relief valve 22 and a pressure gauge 23 complete the ignition apparatus.

Figure 2:
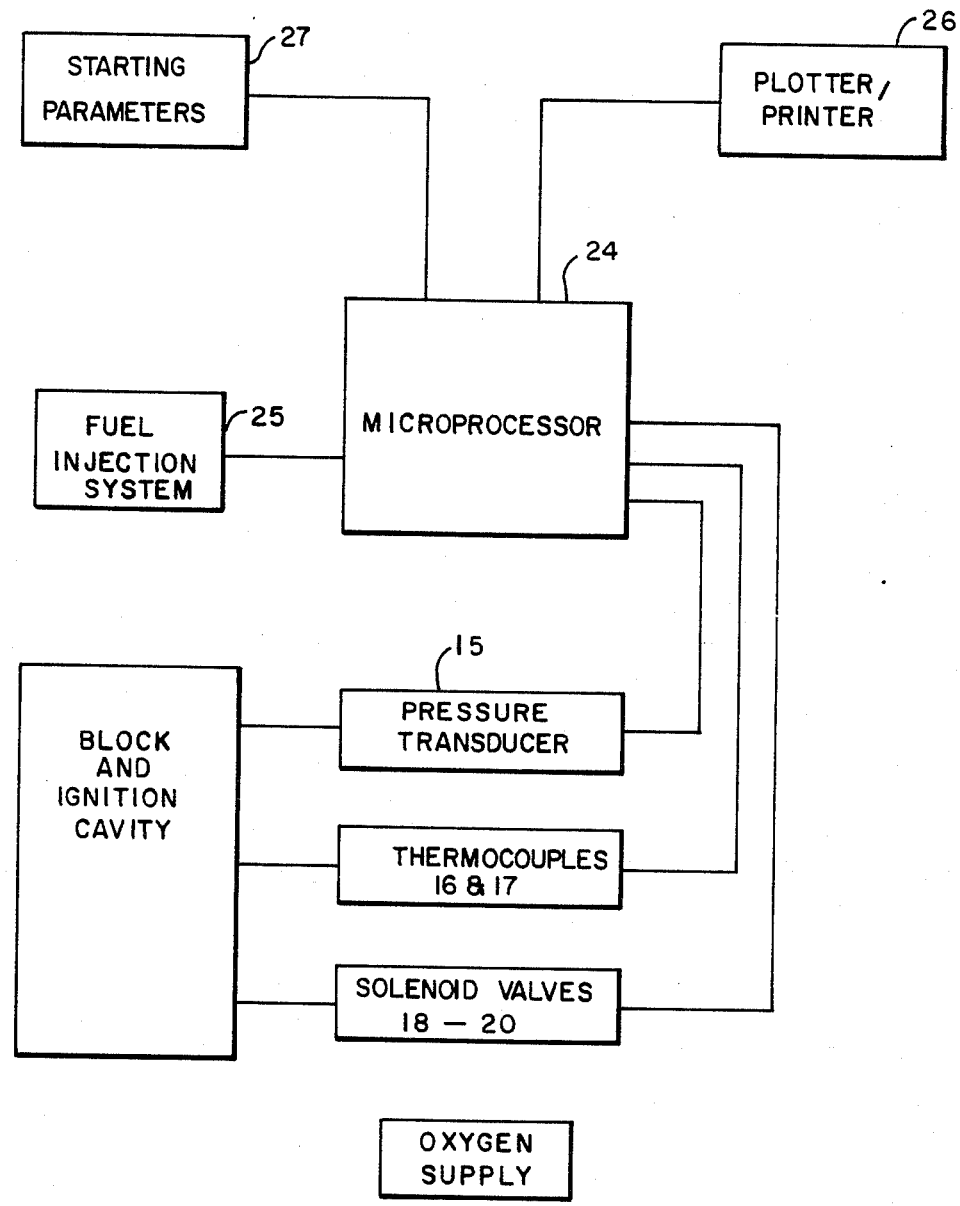
FIG. 2 is a block diagram of the measurement system.

The apparatus is conveniently controlled by a digital computer which also records the data as shown in FIG. 2. Microprocessor 24 controls a fuel injection system 25 (injector) which supplies fuel samples at precise times to the ignition cavity. Pressure transducer 15 and thermocouples 16 and 17 are connected to microprocessor 24 which measures the ignition delay as the time between injection of a sample and ignition as indicated by a peak in measured cavity pressure or cavity temperature. The microprocessor 24 records the ignition delay as a function of cavity temperature prior to fuel injection.

A plotter/printer 26 is provided to produce outputs. An input device 27, such as a keyboard, supplies the starting parameters to the microprocessor.

The operation of the system is as follows. To establish the ignition delay vs. temperature curve for a given fuel, the stainless steel block 11 and the ignition cavity 12 are allowed to equilibrate at $\sim 10$ degrees above the expected ignition temperature. The temperature of the block is then allowed to drop at a steady rate ($\sim 1$ degree/3 minutes) through the duration of the experiments. The injector 25 is a 1 ml syringe filled with the fuel under investigation with the syringe needle inserted into the injection cavity through the injection port. The injector 25 is a simple, auto injector that accurately injects 1/50th of the volume of the syringe upon actuation by the controlling microprocessor 24.

The microprocessor 24 requests the starting parameters of the run, i.e., the starting temperature, number of data points desired, and the temperature interval between data points. It then monitors the cavity and block temperatures until the desired starting temperature has been obtained. The three solenoid valves 18-20 are open throughout this phase, maintaining a flush of pure oxygen through the system. As soon as the starting temperature has been obtained, the three valves 18-20 are closed in sequence, and over the next 12 seconds the average temperature of the cavity is accurately measured. The injector is then actuated, injecting 20 microliters of fuel into the cavity. An electronic timer in microprocessor 24 is simultaneously started and the cavity pressure, temperature, and time are monitored in a rapid response loop. Ignition is recognized by the microprocessor 24 by the extremely sharp pressure and temperature spikes registered upon initiation of combustion. The average cavity temperature just prior to injection and the time interval between injection and ignition (i.e., the ignition delay) are printed.

The solenoid valves 18–20 are reopened, and the products of combustion flushed out by the stream of fresh oxygen. The microprocessor 24 once again starts to monitor the cavity temperature, until the next desired temperature is reached, when the process is repeated. An ignition delay of 40 seconds was chosen as defining no ignition. The microprocessor 24 continues the experiment until three successive no ignition conditions have been registered before halting the run. The microprocessor also handles data manipulation, reduction and tabulation. The final output is an auto-scaled plot of the ignition delay vs. cavity temperatures.

Once the initial parameters have been defined and the fuel is loaded into the syringe, the unit requires no operator attention. If there is no possibility of an educated guess of the unknown fuel's ignition temperature, a rapid prior scan may be performed over a wide temperature range (large temperature intervals between data points), to establish the region of interest. The actual experiment can then be carried out, over this smaller temperature range with data points separated by smaller temperature intervals.

Figure 3:
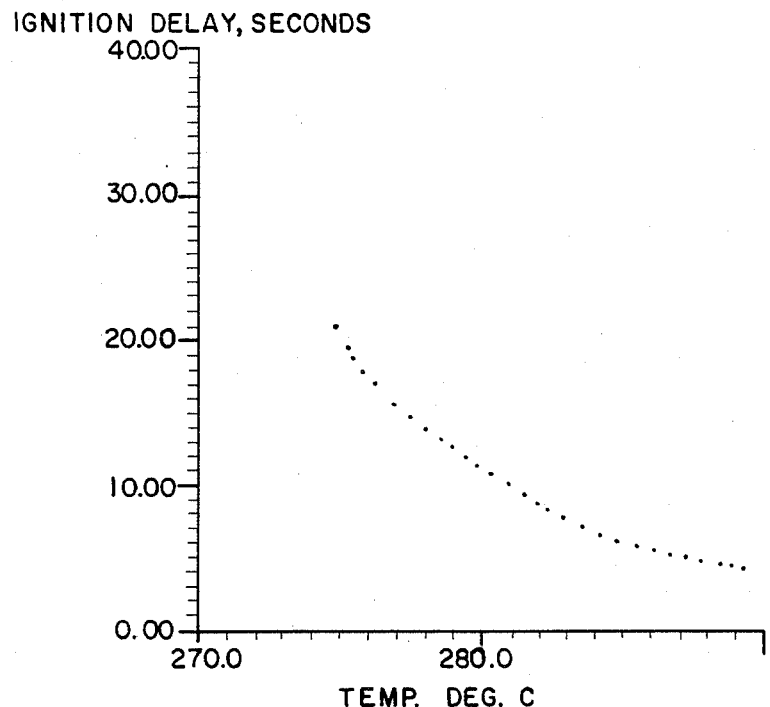
FIG. 3 shows measured ignition delay as a function of temperature.

FIG. 3 is representative of the type of data obtained by the invention. It is seen that there is almost no random scatter of data points. A duplicate run, using the same fuel, was performed a few days later. The two curves superimpose on each other almost exactly, and the agreement between the temperature required for a 20 second ignition delay ($T_{20}$) obtained in the two cases was excellent, indicating the high degree of reproducibility of the data.

A total of 9 samples were analyzed. Seven were straight run No. 2 type diesel fuels (Table 1, Samples 1–8). Two were somewhat lighter jet fuels (Samples 9 and 10). All cetane numbers reported were obtained by outside analyses using the ASTM method.

TABLE 1

| Sample No. | ID | ASTM CN | $T_{20}$ (°C.) |
|---|---|---|---|
| 1 | EMD 1 | 30 | 273.0 |
| 2 | EMD 2 | 28 | 276.2 |
| 3 | EMD 3 | 26 | 280.1 |
| 4 | EMD 4 | 41 | 266.4 |
| 5 | Mobil Heat | 45 | 260.7 |
| 6 | Joliet RM | 27 | 275.9 |
| 7 | MIDW | 61 | 251.7 |
| 8 | Ferndale JA | 42 | 263.7 |
| 9 | P'Boro JA | 46 | 257.7 |

Figure 4:
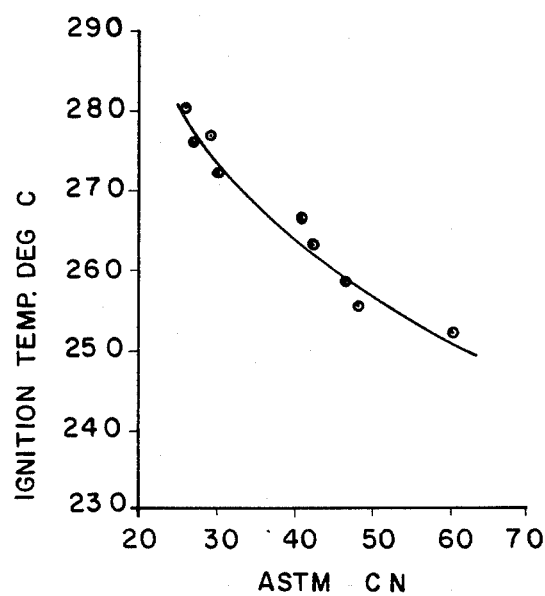
FIG. 4 shows ignition temperature as a function of ASTM cetane number.

FIG. 4 is a plot of the ignition temperature vs. ASTM cetane number for each of the fuels listed in Table 1. The error bar on the ignition temperature measurement is estimated to be no more than ±0.5° C. The normally accepted error bar on cetane number measurement is ±2 CN units as referred to in the ASTM Standard Test. Examining FIG. 4, it is apparent that the ignition temperature of the distillate fuels tested fall on a smooth correlation curve.

Using this correlation curve, the cetane number of four other distillate fuels were estimated and compared with the predictions with the observed ASTM values in Table 2 below. The estimated and ASTM results were in very good agreement.

TABLE 2

| Sample | $T_{20}$ (°C.) | Predicted ASTM CN | Measured ASTM CN |
|---|---|---|---|
| 1 | 280.7 | 24.3 | 25.5 |
| 2 | 277.6 | 26.5 | 28.9 |
| 3 | 269.8 | 34.0 | 34.8 |
| 4 | 261.6 | 44.0 | 46.0 |

Each of the $T_{20}$ temperatures listed in Table 1 was obtained, as discussed above, by first establishing the ignition delay curve ($T_{20}$ versus temperature) for that particular fuel. This necessitates the measurement of a number of $T_{20}$ values at different temperatures. In some cases it may be possible to correlate the ignition delay itself against cetane number, at least over a narrow band of cetane numbers, provided the measurement temperature remained constant at some appropriate value. Eight different blends of CHD product and #2 fuel oil were tested, to encompass a range of approximately 6 cetane units (42.94 to 48.8). The ignition delay of each of these fuel blends measured at a constant temperature of 268° C. (±0.3° C.), is plotted against the cetane number in FIG. 5. The resultant correlation is very good. Calibration curves of this type may be useful for rapidly detecting small deviations of the cetane quality of refinery streams from a specified value, or for use at a blending terminal to establish the desired cetane rating.

In an exemplary embodiment of the invention, the block 11 was a stainless steel cylinder with a diameter of 4.5 inches and a height of 6.5 inches. The ignition cavity 12 was 1.5 inches deep. Microprocessor 24 was a Hewlett Packard HP9825B and fuel injector 25 was a "repeating dispenser" supplied by Supelco, Inc., Bellefont, PA, Catalog No. 2-0943.

While a particular embodiment of the invention has been shown and described, various modifications are within the true spirit and scope of the invention. The appended claims are, therefore, intended to cover all such modifications.

What is claimed is:

1. Apparatus for measuring the ignition delay of distillate fuel comprising:
   a block having an ignition cavity;
   means for heating said block to an elevated temperature above the ignition temperature of said fuel so that the temperature in said cavity is substantially uniformly the same temperature as said block;
   means for injecting samples of said fuel into said ignition cavity as said block cools from said elevated temperature;
   means for measuring the pressure in said cavity;
   means for measuring the temperature in said cavity;
   a digital computer having:
      means for controlling the time of injection of said samples;
      said pressure and temperature measuring means being connected to said digital computer:
      means in said digital computer for measuring ignition delay as the time between the injection of a sample and ignition as indicated by a peak in measured cavity pressure or temperature;
      means for recording said ignition delay as a function of the cavity temperature when ignition occurred; and
   solenoid valves actuated by said digital computer for flushing and exhausting said cavity, said valves being closed during injection and ignition of a sample and thereafter being opened to flush said cavity before injection of another sample.

2. The apparatus recited in claim 1 wherein said solenoid valves include a first valve between a source of oxygen and said cavity and a second valve between said cavity and atmosphere so that oxygen flushes said cavity when said valves are open.

3. The apparatus recited in claim 2 further comprising:
a third solenoid valve between said source of oxygen and said pressure transducer for supplying said pressure transducer with reference pressure oxygen when said valves are open.

4. A method of measuring the cetane number of distillate fuel comprising:
heating a block having an ignition cavity to an elevated temperature above the ignition temperature of said fuel so that the temperature in said cavity is substantially uniformly the same temperature as said block;
repeatedly injecting samples of said fuel into said ignition cavity as said block cools from said elevated temperature;
measuring the pressure in said cavity;
measuring the temperature in said cavity;
automatically controlling the time of the injection of said samples with a digital computer;
measuring ignition delay with said digital computer as the time between injection of a sample and ignition as indicated by a peak in measured cavity pressure or temperature;
correlating said ignition delay with cetane number to indicate the cetane number of said sample;
flushing out the cavity selectively before injection of the samples.

5. The method recited in claim 4 further comprising:
measuring ignition delay of fuels of known cetane number at a constant temperature;
calibrating ignition delay as a function of cetane number for said constant temperature; and thereafter
measuring ignition delay of fuels of unknown cetane number at said constant temperature.

6. The method recited in claim 5 further comprising:
estimating the cetane number of said unknown fuels from the calibration of ignition delay as a function of cetane number.

7. The method recited in claim 4 further comprising:
plotting ignition delay as a function of the temperature at which ignition occurred.

8. The method recited in claim 4 further comprising:
determining the ignition temperature at which a predetermined ignition delay occurred; and
selecting the cetane number associated with the determined ignition temperature.

* * * * *